US00PP31586P3

(12) United States Plant Patent
Dirr et al.

(10) Patent No.: US PP31,586 P3
(45) Date of Patent: Mar. 24, 2020

(54) CRAPEMYRTLE PLANT NAMED 'DJ 05-14'

(50) Latin Name: ***Lagerstroemia* hybrid**
Varietal Denomination: DJ 05-14

(71) Applicant: University of Georgia Research Foundation, Inc., Athens, GA (US)

(72) Inventors: Matthew A. Dirr, Watkinsville, GA (US); Donglin Zhang, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/350,966

(22) Filed: Feb. 5, 2019

(65) Prior Publication Data

US 2019/0246542 P1 Aug. 8, 2019

Related U.S. Application Data

(60) Provisional application No. 62/627,054, filed on Feb. 6, 2018.

(51) Int. Cl.
*A01H 5/00* (2018.01)
*A01H 6/00* (2018.01)
*A01H 5/02* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./252
CPC ..... A01H 5/00
See application file for complete search history.

(56) References Cited

U.S. PATENT DOCUMENTS

PP27,194 P3 * 9/2016 Helvick ..... Plt./252

* cited by examiner

*Primary Examiner* — Annette H Para
(74) *Attorney, Agent, or Firm* — Klarquist Sparkman, LLP

(57) ABSTRACT

A new crapemyrtle plant has deep, uniform purple foliage and stems; a light lavender to white flower color; an intermediate upright growth habit; and powdery mildew and Cercospera resistance.

2 Drawing Sheets

Latin name of the genus and species of the plant claimed: 'DJ 05-14' is a Crapemyrtle plant that is a *Lagerstroemia* hybrid.

Variety denomination: The new crapemyrtle plant claimed is a variety denominated 'DJ 05-14'.

BACKGROUND OF THE INVENTION

The present invention relates to the discovery of a new and distinct cultivar of the ornamental flowering shrub *Lagerstroemia indica* x *Lagerstroemia fauriei*, commonly known as crapemyrtle, and hereafter referred to by the varietal denomination 'DJ 05-14', as herein described and illustrated.

The new crapemyrtle originated from open pollinated seed of a patented plant, 'Chocolate Mocha' Crapemyrtle (U.S. Plant Pat. No. 21,540). 'DJ 05-14' was selected from plants grown at a horticulture farm in Watkinsville, Ga. The seedlings were planted in containers and selections were made for plants based on the following criteria:

1.) Intermediate, upright growth habit
2.) Powdery mildew resistance
3.) Flower color and quality
4.) Deep purple foliage and stem color 'DJ 05-14' was selected in September 2014.

Asexual reproduction by traditional vegetative cuttings since 2014 at the horticulture farm in Watkinsville, Ga. has shown that the distinguishing characteristics of the new crapemyrtle variety, 'DJ 05-14' are stable and reproduced true to type in successive generations.

SUMMARY OF THE INVENTION

'DJ 05-14' has not been observed under all possible environmental conditions. The phenotype may vary somewhat with changes in light, temperature, soil and rainfall amount, however, any variance in genotype.

The following traits have been observed and represent the characteristics of the new cultivar. Asexual propagation by cuttings has proven that these characteristics are firmly fixed in succeeding asexually propagated generations. In combination, these characteristics distinguish 'DJ 05-14' from all other varieties known to the inventor:

1.) Deep, uniform, purple foliage and stems;
2.) Light lavender and white flower color;
3.) Intermediate, upright growth habit; and
4.) Powdery mildew and Cercospera resistance.

'DJ 05-14' is distinguished from its parent plant *Lagerstroemia indica* x *Lagerstroemia fauriei* 'Chocolate Mocha' by its improved, more consistent, deeper purple foliage and its larger, light lavender and white flowers. 'DJ 05-14', after over 3 years of evaluation, has proven to be more resistant to powdery mildew and cercospera than 'Chocolate Mocha'.

DESCRIPTION OF THE DRAWINGS

The accompanying colored photographic illustrations show the overall appearance and distinct characteristics of the new 'DJ 05-14' cultivar. The colors in the photographs are as close as possible with the photographic and printing technology utilized.

DETAILED DESCRIPTION

Figure 1:
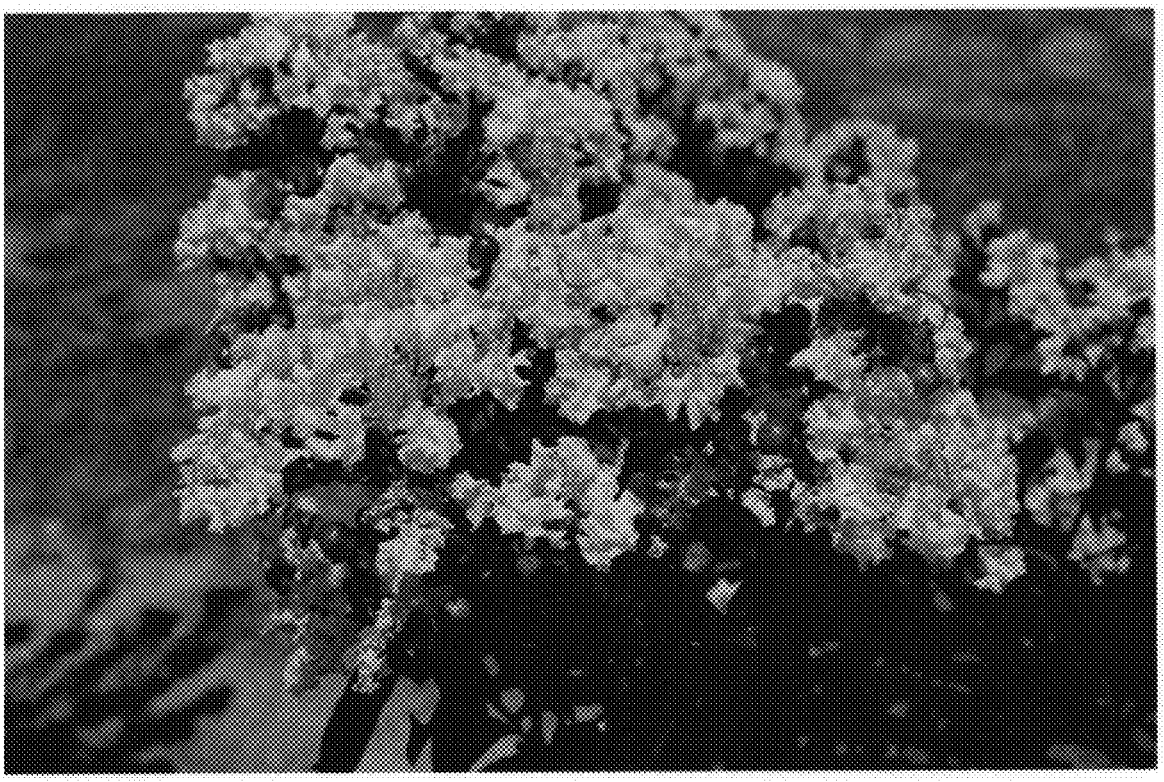
FIG. 1 is a close up view of the flowers of the 'DJ 05-14' variety.
Figure 2:
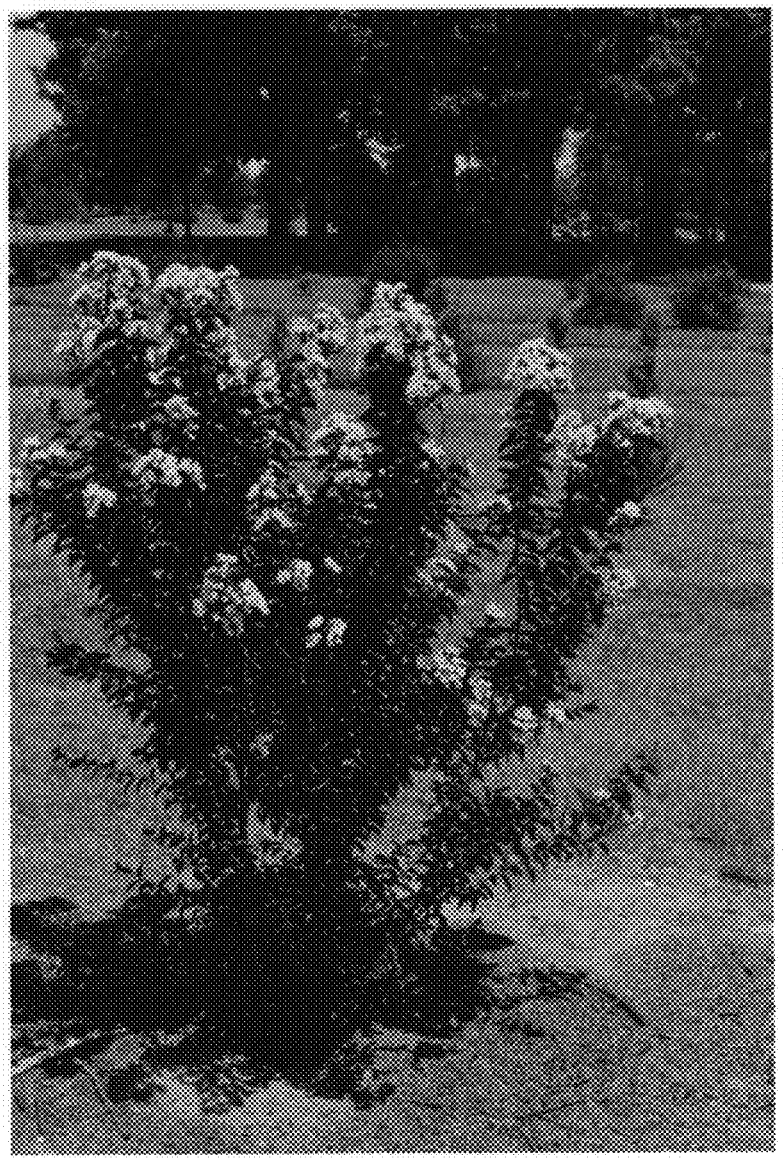
FIG. 2 is a view of the 'DJ 05-14' plant.

In the following description, color references are made to The Royal Horticulture Society Colour Chart, 2015 Edition, except where general terms of ordinary dictionary significance are used. Plants used for the description were approximately 2.5 years old and grown in 11.4 liter containers in full sun at the horticulture farm in Watkinsville, Ga.

Botanical/plant Description: 'DJ 05-14' is a cultivar of *Lagerstroemia indica* x *Lagerstroemia fauriei* 'Chocolate Mocha'. The current variety is a progeny from seed collected from 'Chocolate Mocha' in November of 2013. Male, or pollen parent, is unknown (open-pollinated).

*General description.*—Flowering shrub (normal growth type); compact, upright, intermediate growth habit. Freely branching; lateral branches abundant without pruning (although some winter pruning of dead wood is recommended). Ultimately, proper pruning will result in a fine-textured, dense habit.

*Plant size.*—The original plant has been in the ground for 3.5 years, is 152 cm high from the soil level to the top of the uppermost inflorescences and about 91 cm wide.

Propagation:

*Vegetatively by terminal cuttings. Time to initiate roots during summer takes about* 21 *days at* 32 *degrees C.*

*Flowering shrub; compact, upright, intermediate growth habit. Freely branching; lateral branches abundant without pruning* (*although some winter pruning of dead wood is recommended*). *Ultimately, proper pruning will result in a fine-textured, dense habit.*

*Blooming period.*—June-September in Watkinsville, Ga. Rebloom after 6-8 weeks when spent flowers are removed.

*Plant type.*—Deciduous flowering shrub.

*Plant habit.*—Compact, branching, upright in outline, finely textured, freely branched without pruning. Height and spread, about 2.4 meters in height and 1 meter in width.

*Cold hardiness.*—USDA zones 6-8.

*Disease and pests.*—Resistant to powdery mildew (caused by erysiphe Lagerstroemiae) and cercospera leaf spot (cercospera lythracearum) have been observed.

*Root description.*—Numerous fibrous and well branched, color 155D; young roots are fibrous where old roots are woody.

*Root development.*—Average 6 weeks at 25 degrees C. for root initiation and average 3 months at 30 degrees C. to produce a young rooted plant Softwood stem cuttings root readily at 20-25 degrees C.

*Growth rate is moderate.*

Branch description:

*Branch shape.*—Tetragonal on first year growth, round on second year growth.

*Branch color.*—First year N79B; Second year 199D; trunk is 199E.

*Branch size.*—Main branch: first year 30 cm in length and 5 mm in diameter; Second year 60 cm in length and 8 mm in diameter, lateral branches are 60-70 cm in length and 1.5 cm in diameter, Trunk; multi branched and 2.5 cm in diameter at the soil level.

*Branch surface.*—Lateral branches sparsely covered with irregular lenticals 177B in color, trunk fine, smooth barked.

*Branch strength.*—Young; flexible but strong, mature; easily snapped.

*Branching.*—Freely branching habit without pruning, average of 8 lateral branches.

*Branching aspect.*—Held at angles between 30 to 60 degrees, internode length average at 2 cm.

*Vegetative buds.*—Alternate sub-opposite in arrangement, average of 4 mm in length and 3 mm in width, conical in shape 5-scaled imbricate and lack pubescence, color N79B.

Foliage description:

*Leaf shape.*—Elliptic, leaf division is single (simple).

*Leaf base.*—Cuneate.

*Leaf apex.*—Acute to abruptly acuminate.

*Leaf veination.*—Pinnate, upper surface color N186A, lower surface color N187D.

*Leaf margins.*—Entire.

*Leaf arrangement.*—Sub-opposite to alternate.

*Leaf attachment.*—Petiolate.

*Leaf surface.*—Upper surface glossy; lower surface dull, slightly pubescent.

*Leaf size.*—Average 3.5 cm in length and 2 cm in width.

*Leaf quantity.*—Average 76 per lateral branch.

*Leaf color.*—Young upper surface N186A, young lower surface N187B; mature upper surface N186A, mature lower surface N187B.

*Petiole.*—Average 1 mm in length and 1 mm in diameter, surface texture smooth; color N186B, moderate strong.

Flower description:

*Inflorescence type.*—Terminal panicle, 14 thyrses, thyrses are pyramidal conical and 5 mm long.

*Persistence of inflorescence.*—Inflorescence are showy for an average of 4 weeks, individual flowers persist for an average of 2 days, self cleaning.

*Inflorescence size.*—An average of 25 cm n height 15 cm in width.

*Inflorescence number.*—Terminally borne, 1 per lateral branch.

*Flower number.*—Average of 10 flowers and flower buds per inflorescence.

*Flower fragrance.*—Light sweet scent.

*Flower buds.*—Globose in shape, an average of 5 mm in width and 8 mm in length, obovate, rounded apex, surface is lustrous with 6 distinct suture lines, color 61A.

*Flower aspect.*—Upright to outward.

*Flower type.*—Actinomorphic.

*Flower size.*—Average of 2 cm in height and 1.3 cm in diameter.

*Petals.*—Typically 6, rotate, whorled in arrangement, fan shaped, ruffled margins, sagittate base, ruffled and rounded apex. Both surfaces glabrous, an average of 1 cm in length and 3.2 cm wide, color 77C.

*Calyx.*—Consists of 6 sepals fused at base, narrowly triangular in shape, typically 7 mm long and 10 mm wide, apex is acuminate, entire margin, fine texture, smooth and glabrous on both surfaces, sepal color 183 top and N144C bottom.

*Peduncle*.—Strong, average 7 cm in length and 3 mm in diameter. Surface is covered with fine, appressed pubescence and is strong.

*Pedicels*.—Strong, average of 8 mm in length and 1 mm in diameter, surface is covered with fine appressed pubescence.

Reproductive organs:

*Stamens*.—25-30 stamens clustered in the center, filament length 0.8 cm to 1.8 cm, filament color red purple 63A, 6 mm in length surrounded by 6 longer stamens; stamens are 1 cm in length, glabrous, surface; anthers orbital shape, 1 mm long, color yellow orange group 15B; pollen amount good, color 12B.

*Pistils*.—Single(1) Average of 1.8 mm in length; style — 2 cm in length, color 53B; stigma-globe shaped; less than 1 mm in diameter, color yellow green group 152B; ovary, superior, color yellow group 11B, 3 mm in diameter.

Fruit and seed: Capsule; 6 valved dehiscent, broad rounded in shape. Immature 141C in color, mature N199C in color, each capsule contains 25 seeds on average, seeds 6 mm in length and 3 mm in width and N199B in color, fruit skin color 200A, fruit flesh color 139C, fruit shape-oval rounded, 7 mm in diameter and 9 mm long, fruit depression at apex is absent, fruit depression at the base is absent.

Plant insect resistance: Neither resistance to or susceptibility to normal pests of *lagerstroemia* plants has been observed.

We claim:

1. A new and distinct cultivar of the Crapemyrtle plant named 'DJ 05-14', as herein illustrated and described.

* * * * *